US008629401B2

(12) United States Patent  
Kaskel et al.

(10) Patent No.: US 8,629,401 B2
(45) Date of Patent: Jan. 14, 2014

(54) METHOD AND DEVICE FOR DETERMINING THE ADSORPTION OF A GAS ON MATERIALS

(75) Inventors: Stefan Kaskel, Dresden (DE); Philipp Wollmann, Dresden (DE); Matthias Leistner, Dresden (DE)

(73) Assignee: Fraunhofer-Gesellschaft zur Förderung der angewandten Forschung e.V. (DE)

( * ) Notice: Subject to any disclaimer, the term of this patent is extended or adjusted under 35 U.S.C. 154(b) by 11 days.

(21) Appl. No.: 13/380,352

(22) PCT Filed: Jun. 22, 2010

(86) PCT No.: PCT/DE2010/000756
§ 371 (c)(1),
(2), (4) Date: Mar. 12, 2012

(87) PCT Pub. No.: WO2010/149152
PCT Pub. Date: Dec. 29, 2010

(65) Prior Publication Data
US 2012/0168628 A1    Jul. 5, 2012

(30) Foreign Application Priority Data

Jun. 26, 2009   (DE) .......................... 10 2009 031 764

(51) Int. Cl.
*G01J 5/02* (2006.01)
(52) U.S. Cl.
USPC ..................................................... 250/341.6
(58) Field of Classification Search
USPC ................... 250/340, 341.1–341.8, 342–352
See application file for complete search history.

(56) References Cited

U.S. PATENT DOCUMENTS

2005/0082482 A1   4/2005   Ludviksson

FOREIGN PATENT DOCUMENTS

DE    4431932 A1    5/1996
DE    10019122 A1   10/2001
(Continued)

OTHER PUBLICATIONS

Rege et al., "A novel FTIR method for studying mixed gas adsorption at low concentrations: H2O and CO2 on NzX zeolite and gamma-alumina," 2001, Chemical Engineering Science, vol. 56, pp. 37812-3796.*
"International Application No. PCT/DE2010/000756, International Preliminary Report on Patentability issued Jan. 17, 2012", (w/ English Translation of the Written Opinion), 6 pgs.

(Continued)

*Primary Examiner* — Kiho Kim
(74) *Attorney, Agent, or Firm* — Schwegman Lundberg & Woessner, P.A.

(57) ABSTRACT

The invention relates to a method and to an apparatus for determining the adsorption of a gas at materials. It is the object of the invention to propose possibilities for the determining of the surface properties of materials in which statements can be obtained and very small sample volumes can be examined with sufficient measurement precision, with a reduced technical plant effort and with a reduced time effort. In the invention, a sample of a material is acted on by a gas or gas mixture within a chamber which is not transparent for electromagnetic radiation in the wavelength range between 150 nm and 25 μm. The gas or at least a gas included in a gas mixture is adsorbed at the surface of the sample and in this respect the electromagnetic radiation emitted by the sample as a consequence of the adsorption is detected by at least one optical detector which is sensitive at least in a range of the wavelength range between 150 nm and 25 μm. The measured signals of the detector(s) are in this respect detected with time resolution and are evaluated within a predefinable time interval for determining the surface temperature and/or the adsorption heat of the respective sample varying due to the adsorption.

19 Claims, 2 Drawing Sheets

(56) References Cited

FOREIGN PATENT DOCUMENTS

Figure 1:
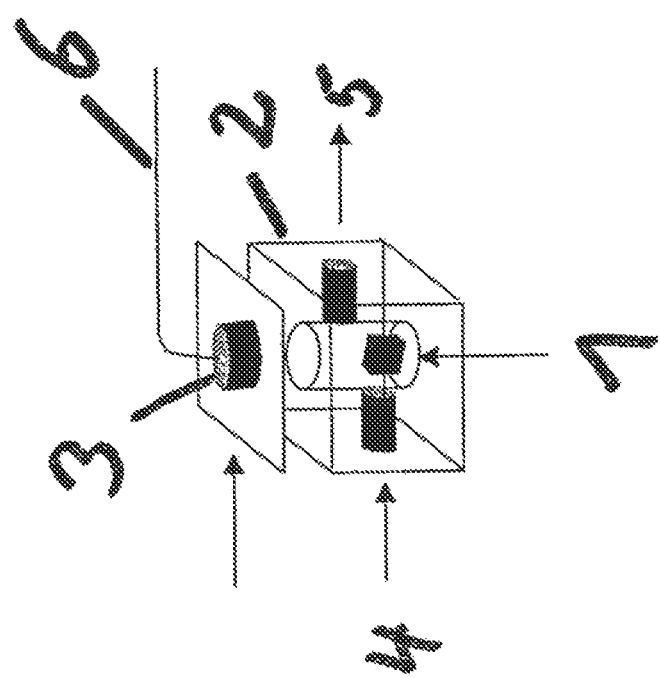

| | | |
|---|---|---|
| EP | 0260942 | 3/1988 |
| EP | 1775015 A1 | 4/2007 |

OTHER PUBLICATIONS

"International Application No. PCT/DE2010/000756, International Search Report and Written Opinion mailed Nov. 12, 2010", 13 pgs.

* cited by examiner

METHOD AND DEVICE FOR DETERMINING THE ADSORPTION OF A GAS ON MATERIALS

PRIORITY CLAIM TO RELATED APPLICATIONS

This application is a national stage application under 35 U.S.C. §371 of PCT/DE2010/000756, filed Jun. 22, 2010, and published as WO 2010/149152 A1 on Dec. 29, 2010, which claims priority to German Application No. 10 2009 031 764.3, filed Jun. 26, 2009, which applications and publication are incorporated by reference as if reproduced herein and made a part hereof in their entirety, and the benefit of priority of each of which is claimed herein.

The invention relates to a method and to an apparatus for determining the adsorption of a gas at materials. In this respect, a conclusion can be drawn on the material properties such as the surface, porosity or affinity to gases. Statements on the adsorption behavior of materials with respect to gases or gas mixtures can also be acquired, which can be of importance, for example, for the separation of individual gases from gas mixtures.

The properties in question are frequently of interest in newly developed materials or materials manufactured in a new form. However, carrying out corresponding examinations in order, for example, to be able to determine the affinity of materials to gases causes problems and is associated with a high effort and/or cost.

In the past, the adsorption heat had been determined calorimetrically and gravimetric measurements had also been carried out. The last named measurements, however, require highly precise measuring technology since the change of the mass by the adsorption of a gas at the material surface is extremely low.

The adsorption heat was determined calorimetrically using Tian-Calvet calorimeters or a process and measurement setup described in DE 100 19 122 A1. In this respect, since the temperature variations occurring due to adsorption are relatively small, a substantial metrological effort with a plurality of temperature sensors and a great effort and/or cost for the thermostatting are required. The required time effort is also high since the measurements last at least several hours. A minimum sample volume is required.

These previously known solutions are therefore only suitable with restrictions for fast investigations, in particular comparative investigations, which are obtained at newly developed materials or those which are obtained with new or modified manufacturing processes.

It is therefore the object of the invention to propose possibilities for determining the surface properties of materials in which statements can be obtained with sufficient measurement accuracy and with a reduced technical plant effort and time effort and in which very small sample volumes can be examined.

This object is achieved in accordance with the invention by a method in accordance with claim 1. The determination can be carried out using an apparatus which has the features of claim 15. Advantageous embodiments and further developments of the invention can be achieved with the use of features designated in subordinate claims.

In the invention, a sample of a material is arranged within a chamber. The chamber is not transparent for electromagnetic radiation in the wavelength region between 150 nm and 25 µm. A gas or gas mixture is supplied so the chamber and she sample is acted on by it so that the gas or at least a gas included in a gas mixture is adsorbed at the surface of the sample to determine the adsorption of a gas at the sample material. Since a heating takes place in the adsorption, this temperature increase can be measured. At least one optical detector is arranged in the chamber for this purpose. The detector is at least sensitive in a range of the wavelength range between 150 nm and 25 µm. Infrared sensors are preferably used. The electromagnetic radiation emitted by the sample as a consequence of the adsorption can be detected by the detector(s). The detected measured signals of the detector(s) are in this respect detected with time resolution and are evaluated within a predefinable time interval for determining the surface temperature and/or the adsorption heat of the respective sample varying due to the adsorption.

The respective adsorbing gas or gas mixture should be supplied to the chamber, and thus also to the sample, over a predefinable time with a controlled and/or regulated partial pressure. This can be achieved by a direct influencing of the volume flow via a gas supply into the chamber.

The maximum temperature which has occurred as a consequence of the adsorption and/or, due to an integration of the detected measured signal within a predefined time interval, the respective adsorption heat can be utilized for the evaluation or also for a comparison of different samples.

A plurality of samples can in particular be simultaneously exposed to an adsorbing gas or to a gas mixture flow including such a gas in a chamber for comparative examinations or also to increase the evaluation precision. In this case, at least one detector is associated with each sample.

A plurality of detectors can also be associated with a sample. In this respect, the detectors should be aligned or arranged so that different surface regions of the sample are detected. They can be wholly or partly different surface regions if, for example, a detection is made from different directions. There is, however, also the possibility of detecting a smaller surface region with one detector and a larger surface region, in which the smaller surface region is included, with a further detector. In this respect, the same detectors can be arranged at different distances from the sample surface or a setting of an optical system allowing a specific focal length can be present at least one detector.

The detectors used can be selected or designed such that they are sensitive for specific wavelengths or wavelength ranges and they are then only taken into account in the measurement. Suitable optical filters, for example band pass filters or edge filters, can be arranged between the detector and the sample for this purpose. Adjustable detectors (infrared Fabry-Perot interferometers) can also be used. They can be adjusted to a wavelength or to a tightly restricted wavelength interval which is particularly suitable for the measurement. The measured signal can thereby have a smaller portion of disturbance variables.

A procedure can be followed in the determination such that first, that is before the actual determination is carried out, a non-adsorbing gas or an only slightly adsorbing gas is continuously conducted through the chamber. After a predefinable time, a gas adsorbing at the sample is admixed to this gas at a constant partial pressure over a predefined time interval. The temperature increase occurring due to the adsorption has the result that electromagnetic radiation is emitted from the sample which can be detected and measured using the at least one detector. As a rule, the measured signal is an electric voltage which is proportional to the temperature and which can be detected over time.

Nitrogen, helium or hydrogen can be used as a non-adsorbing gas or as an only slightly adsorbing gas and methane, alkanes having the general formula $C_nH_{2n+2}$ such as ethane, propane, $CO$, $CO_2$, $H_2O$, $NO_x$, $NH_3$, $H_2S$ or butane can be used as an adsorbing gas. Further absorbing gases can be alkenes, alkines or polyenes. Solvent vapors of aromats such as benzole, toluol, ketones (acetone), esters or thiols or also alcohol (vapors) can, however, also be examined in their stead.

The supplied gas or gas mixture should be brought to the right temperature before it is supplied into the chamber for the determination. In contrast to the known technical solutions, a process can take place at normal environmental temperatures, that is work can be carried out at room temperature. It is, however, also possible to set temperatures of up to 120° C., preferably up to 100° C. and also a temperature of approximately 77 K. Nitrogen, argon and hydrogen can be used as the adsorbing gas at this temperature and helium can in this respect be used as the non-adsorbing gas or only slightly adsorbing gas. The temperature should merely be kept constant. A heating device which can be regulated can be present at a gas supply to the chamber for this purpose.

There is the possibility of ending the supply of gas or of a gas mixture subsequent to a carried out adsorption and then determining the released initially adsorbed as volume with a simultaneous energy supply. The energy supply can take place by means of a heating device integrated into the chamber. In this respect, a sample can be arranged at such a heating device or the energy supply can be achieved by irradiating with electromagnetic radiation.

Previously activated samples should advantageously be inserted into the chamber. An activation of the samples can also be achieved within the chamber by supply of a non-adsorbing gas or of an only slightly adsorbing gas heated to a temperature above 50° C., preferably at 70° C.

The examinations in question can be carried out with the invention within a comparatively short time which does not exceed 20 min and is shorter as a rule. As already addressed, a plurality of samples can be taken into account simultaneously and the determination can be carried out together. Very small samples can be examined. Samples having a deadweight of a few mg (approx. 2 to 20 mg) can be examined. In this respect, it should only be considered that where possible only electromagnetic radiation emitted by one sample is imaged at a detector and that this is measured.

Due to the advantages achieved, the invention can in particular be used for fast tests in which the basic suitability of new materials can be determined or materials manufactured using a new manufacturing process or one which is to be optimized can be examined and improved. The examinations do not have to be carried out at highly reduced or elevated pressures and temperatures. The effort for the thermal insulation is small since the required measurement time can be kept small in comparison with the prior art. It should only be considered that no electromagnetic radiation or electromagnetic radiation which interferes only slightly occurs within the chamber which does not occur as a consequence of the adsorption. For the case that interfering electromagnetic radiation cannot be completely avoided, there is the possibility of excluding it in the measurement by optical filters or of carrying it out by a setting of an adjustable detector so that it is not sensitive at the interfering wavelengths.

The invention will be explained in more detail by way of example in the following.

Figure 2:
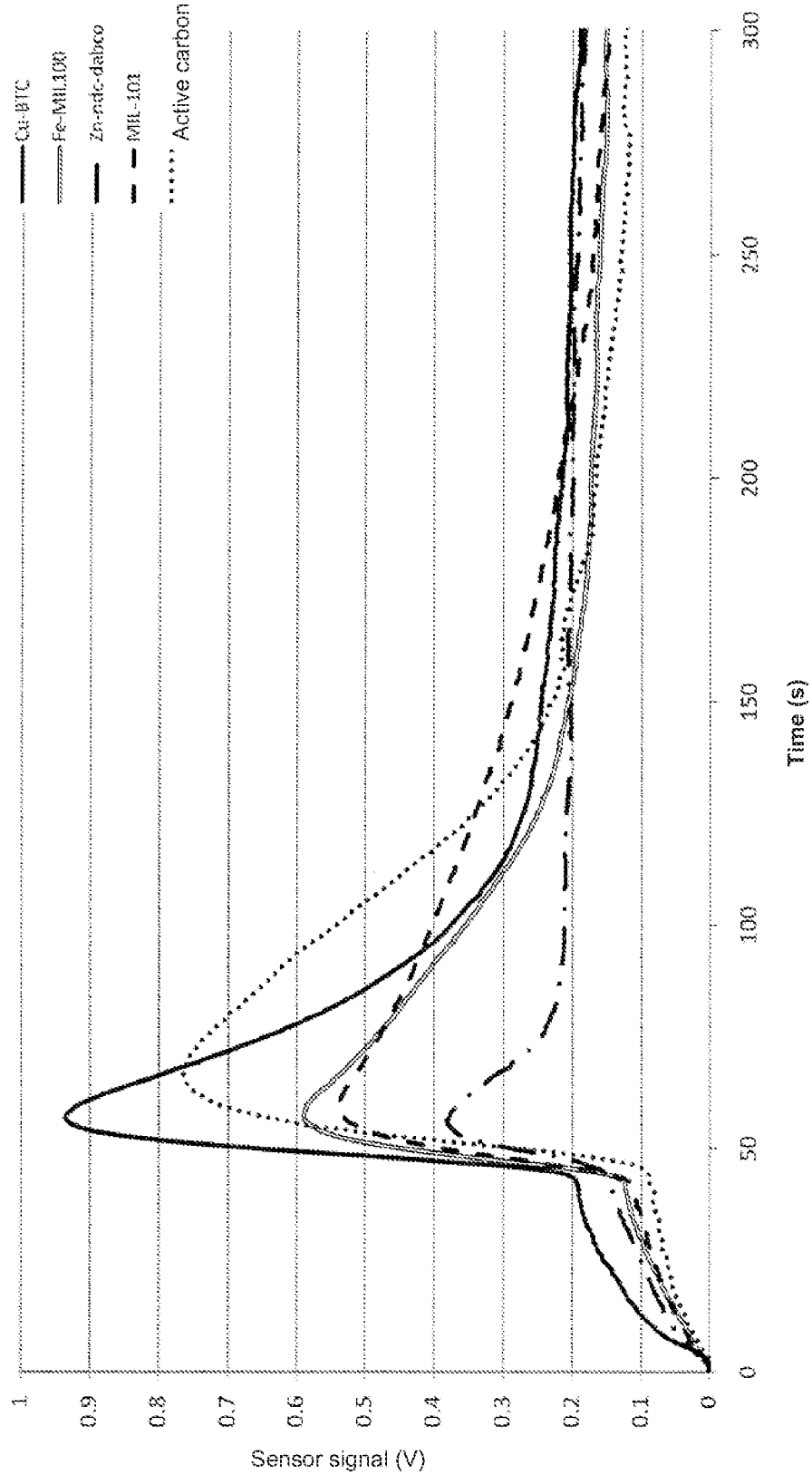

There are shown:

FIG. 1 the setup of an apparatus in accordance with the invention in schematic form; and FIG. 2 a diagram by which examinations at different samples are illustrated by way of comparison.

The basic structure of an apparatus suitable for examinations to be carried out in accordance with the invention is shown schematically in FIG. 1.

In this example, only one sample 1 and one optical detector 3, which is here an infrared sensor with a sensitivity in the wavelength range from 5 µm to 20 µm, are arranged in a chamber 2 closed at all sides with the exception of a gas supply 4 and a gas outlet 5. The chamber 2 is formed from a non-transparent material.

The detector 3 is connected via a measured signal line 6 to an electronic evaluation unit not shown here.

After the insertion of a sample 1 into the chamber 2 and the closure thereof, an activation of the sample material took place by the supply of nitrogen via the gas supply 4 which, has been heated to a temperature of 70° C. The activation was carried out over a time of 30 min.

Subsequent thereto, pure nitrogen was introduced into the chamber at a constantly maintained temperature of 23° C. with a volume flow of 30 ml/ml over a time of 30 s and was then removed again via the gas outlet 5. The chamber 2 had a free inner volume of 0.5 cm$^3$.

At the end of this time, butane was admixed to the nitrogen using a metering device before the inlet into the chamber 2. A volume flow of 30 ml/min was set for nitrogen and 10 ml/min for butane. Other ratios and volume flows can, however, also be used for the examinations.

Comparative examinations were carried out using samples 1 made of five different materials.

In this case, these were the following materials:

MIL-100$_{Fe}$ Fe$_3$F(H$_2$O)$_3$O[C$_5$H$_3$—(CO$_2$)$_3$]$_2$nH$_2$O
MIL-101 Cr$_3$F(H$_2$O)$_2$O[(O$_2$C)—(C$_6$H$_4$)—(CO$_2$)]$_3$nH$_2$O
Cu-BTC Cu$_3$(C$_5$H$_3$(CO$_2$)$_3$)$_2$(H$_2$O)$_3$
Zn-NDC-dabco Zn$_2$[C$_{10}$H$_6$(CO$_2$)$_2$]$_2$—C$_5$H$_{12}$N$_2$
and
active carbon.

The measured signal curves over time detected using the detector 3 are shown for the five materials in the diagram of FIG. 2. The mass of the five samples was 20 mg in each case.

It was found that after a short time from around 50 s the respective maximum was reached and subsequently a decay phase occurred as a consequence of saturation.

The measured signal curves correspond to the respective temperatures at the sample surface which increased accordingly by the adsorption of the butane at the sample surface.

The smallest measurement errors in the evaluation of the respective maximum measured signal and its integral over time up to the reaching of the starting value of the measured signal before the start of the admixture of butane were able to be detected for the evaluation of the individual samples 1. Comparative examinations using butane scales were carried out for this purpose. The integral is proportional to the respective adsorption heat or to the capacity of the adsorbent with respect to butane.

The increase up to the reaching of the maximum value, the time up to the reaching of the starting value or the increase of the measured signal curve starting from the maximum up to the reaching of the starting value can, however, also be used for the evaluation.

A desorption of the samples 1 was carried out subsequent to these adsorption examinations. In this respect, pure nitrogen heated to 70° C. was first conducted into the chamber 2 and out of it again. In this respect, 60 ml/min was introduced over a time of 30 min.

The invention claimed is:

1. A method for determining the adsorption of a gas at materials, wherein a sample of a material within a chamber which is not transparent for electromagnetic radiation in the wavelength range between 150 nm and 25 µm is acted on by a gas or gas mixture, said gas or a gas included in a gas mixture being adsorbed at the surface of the sample; in this respect the electromagnetic radiation emitted by the sample as a consequence of the adsorption is detected by at least one optical detector which is sensitive at least in a range of the wavelength range between 150 nm and 25 µm; and the measured signals of the detector(s) are detected with time resolution and are evaluated within a predefinable time interval for determining the surface temperature and/or the adsorption heat of the respective sample varying due to the adsorption.

2. The method in accordance with claim 1, wherein the gas or gas mixture is supplied to the chamber over a predefinable time with a controlled and/or regulated partial pressure.

3. The method in accordance with claim 1, wherein the maximum temperature achieved as a consequence of the adsorption is determined.

4. The method in accordance with claim 1, wherein one or more infrared sensors are used.

5. The method in accordance with claim 1, wherein the adsorption heat is determined using the measured signal(s) by integration within the predefined time interval.

6. The method in accordance with claim 1, wherein different surface regions of the sample are detected using an optical detector.

7. The method in accordance with claim 1, wherein a non-adsorbing gas or an only slightly adsorbing gas is continuously conducted through the chamber and a gas adsorbing at the sample is admixed to this gas at a constant partial pressure over a predefined time interval for determining the adsorption.

8. The method in accordance with claim 6, wherein nitrogen, helium or hydrogen are used as the non-adsorbing gas or only slightly adsorbing gas and alcohol vapor, methane, ethane, propane, CO, $CO_2$, $H_2O$, $NO_x$, $NH_3$, $H_2S$ or butane are used as the adsorbing gas.

9. The method in accordance with claim 7, wherein the gas and gas mixture are controlled to a temperature in the range of environmental temperature up to 120° C.

10. The method in accordance with claim 7, wherein the gas and gas mixture are temperature controlled to normal environmental temperature.

11. The method in accordance with claim 1, wherein the supplied gas and gas mixture are temperature-controlled.

12. The method in accordance with claim 1, wherein a plurality of samples are simultaneously detected within the chamber and are compared with one another.

13. The method in accordance with claim 1, wherein subsequent to a carried out adsorption the supply of gas or of gas mixture is ended and the released previously adsorbed gas volume is determined with a simultaneous energy supply.

14. The method in accordance with claim 1, wherein previously activated samples are introduced into the chamber or samples are activated within the chamber by supply of a non-adsorbing gas or an only slightly adsorbing gas heated to a temperature above 50° C.

15. An apparatus for determining the adsorption of a gas at materials, wherein a gas supply and a gas outlet are present at a chamber which is not transparent for electromagnetic radiation in the wavelength range between 150 nm and 25 µm, and at least two optical detectors sensitive to electromagnetic radiation in the wavelength region between 150 nm and 25 µm are directed to a sample of a material arranged within the chamber at different angles and/or differently sized surface regions are imaged on the at least two optical detectors by optical elements, wherein the at least two optical detectors are connected to an electronic evaluation unit.

16. The apparatus in accordance with claim 15, comprising a plurality of optical detectors with inserted optical filters and/or with at least one adjustable optical detector, wherein different wavelengths can be detected using the plurality of optical detectors.

17. The apparatus in accordance with claim 15, wherein at least one regulating valve and a temperature control device for the gas or the gas mixture supplied to the chamber are present at the gas supply.

18. An apparatus for determining the adsorption of a gas at materials, wherein a gas supply and a gas outlet are present at a chamber which is not transparent for electromagnetic radiation in the wavelength range between 150 nm and 25 µm, and a plurality of optical detectors with inserted optical filters and/or with at least one adjustable optical detector, the plurality of optical detectors sensitive to electromagnetic radiation in the wavelength region between 150 nm and 25 µm, wherein different wavelengths can be detected using the plurality of optical detectors, and wherein the plurality of optical detectors are connected to an electronic evaluation unit.

19. The apparatus of claim 18, wherein at least one regulating valve and a temperature control device for the gas or the gas mixture supplied to the chamber are present at the gas supply.

* * * * *

UNITED STATES PATENT AND TRADEMARK OFFICE
CERTIFICATE OF CORRECTION

PATENT NO. : 8,629,401 B2 Page 1 of 1
APPLICATION NO. : 13/380352
DATED : January 14, 2014
INVENTOR(S) : Kaskel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 85 days.

Signed and Sealed this
Twenty-second Day of September, 2015

Michelle K. Lee
*Director of the United States Patent and Trademark Office*